United States Patent [19]

Reichmann et al.

[11] 4,373,080

[45] Feb. 8, 1983

[54] POLYISOCYANATES, PREPARATION AND USE THEREOF

[75] Inventors: Wolfgang Reichmann, Duesseldorf; Klaus König; Manfred Schönfelder, both of Leverkusen, all of Fed. Rep. of Germany

[73] Assignee: Bayer Aktiengesellschaft, Leverkusen, Fed. Rep. of Germany

[21] Appl. No.: 105,356

[22] Filed: Dec. 19, 1979

[30] Foreign Application Priority Data

Dec. 30, 1978 [DE] Fed. Rep. of Germany ....... 2856864

[51] Int. Cl.$^3$ .................... C08G 18/78; C07C 127/24
[52] U.S. Cl. ................ 528/45; 260/453 AB; 521/159; 521/160; 528/59; 528/67; 525/127
[58] Field of Search ............... 260/453 AB; 528/45, 528/59, 67; 521/159, 160; 525/127

[56] References Cited

U.S. PATENT DOCUMENTS

| 3,124,605 | 3/1964 | Wagner | 260/453 AB |
|---|---|---|---|
| 3,358,010 | 12/1967 | Britain | 260/453 AB |
| 3,441,588 | 4/1969 | Wagner et al. | 260/453 AB |
| 3,824,266 | 7/1974 | Dietrich et al. | 260/453 AB |
| 3,862,973 | 1/1975 | Dietrich et al. | 260/453 AB |
| 3,903,126 | 9/1975 | Woerner et al. | 260/453 AB |
| 3,903,127 | 9/1975 | Wagner et al. | 260/453 AB |
| 4,051,165 | 9/1977 | Wagner | 260/453 AB |
| 4,147,714 | 4/1979 | Hetzel et al. | 260/453 AB |
| 4,220,749 | 9/1980 | Reichmann et al. | 260/453 AB |

FOREIGN PATENT DOCUMENTS

| 1101394 | 3/1961 | Fed. Rep. of Germany . |
| 1043672 | 9/1966 | United Kingdom . |
| 1043673 | 9/1966 | United Kingdom . |
| 1078390 | 8/1967 | United Kingdom . |

*Primary Examiner*—Dolph H. Torrence
*Attorney, Agent, or Firm*—Gene Harsh; Lawrence S. Pope; Thomas W. Roy

[57] ABSTRACT

The present invention relates to a process for the production of specific polyisocyanates by reacting diamines containing hydrogen atoms which are active in the context of the isocyanate addition reaction with excess quantities of organic diisocyanates. The invention also relates to a modification of the above process characterized in that the diamines are reacted first with excess quantities of a first diisocyanate after which the thus obtained reaction product which contains a urea group and a biuret group is reacted in a second stage with a second diisocyanate. The invention also relates to the use of polyisocyanates as the isocyanate component in the production of polyurethane plastics by the isocyanate-polyaddition process.

4 Claims, No Drawings

POLYISOCYANATES, PREPARATION AND USE THEREOF

FIELD OF THE INVENTION

This invention relates to new organic urea and/or polyuret polyisocyanates containing aliphatically or cycloaliphatically bound isocyanate groups, to a process for the preparation thereof and to the use, thereof optionally in blocked form, i.e., blocked with blocking agents for isocyanate groups for the preparation of polyurethane plastics.

BACKGROUND OF THE INVENTION

Polyisocyanates containing biuret groups are known and are used starting materials for high-grade, light-stable lacquers. They may be obtained for example, from diisocyanates and water (German Auslegeschrift No. 1 101 394 or U.S. Pat. No. 3,124,605), hydrogen sulphide (German Auslegeschrift No. 1,165,580), formic acid German Auslegeschrift No. 1,174,760), tertiary alcohols (German Auslegeschrift Nos. 1 543 178 and 1 931 055 or U.S. Pat. Nos. 3,358,010 and 4,051,165) or monoamines (German Offenlegungsschrift No. 2,308,015 and U.S. Pat. No. 3,903,127).

In these conventional processes, amino groups are initially formed from some the isocyanate groups and further reacted with excess diisocyanate via the corresponding urea diisocyanates to form biuret polyisocyanates. The conversion of the isocyanate groups into amino groups is always accompanied by the formation of gaseous secondary products, such as carbon dioxide, carbon monoxide, carbon sulphoxide or olefins, whose elimination may give rise to emission problems. In the heterogeneous reaction of diisocyanates with water, an additional problem lies in the formation of insoluble polyureas which are difficult to separate off. However, the particular disadvantage of these known processes lies in the fact that some of the isocyanate groups, in the diisocyanates used as starting material, are initially destroyed as a result of formation of amino groups.

There has also been no shortage of attempts to produce polyisocyanates containing biuret groups by directly reacting diamines with diisocyanates without any elimination of volatile secondary products and without the destruction of isocyanate groups in amine formation.

On account of the high reactivity of aliphatic amino groups to isocyanate groups, considerable practical difficulties were encountered, because the reaction of primary diamines with diisocyanates has a great tendency to form insoluble polyureas and cross-linked products.

As may be seen from German Offenlegungsschrift No. 2,261,065, for example, uneconomically long afterheating at elevated temperature is required for completing the reaction where readily available starting materials, such as hexamethylene diamine and hexamethylene diisocyanate, are used. This greatly impairs the properties of the end products, particularly the natural color thereof.

According to German Offenlegungsschrift No. 2,609,995 and U.S. Pat. No. 4,147,714, these disadvantages may be obviated by introducing the diamine into the diisocyanate in vapor form under carefully controlled conditions. In this process, however, steps have to be taken to ensure that no diisocyanate enters the feed pipe because otherwise blockages attributable to urea formation may rapidly occur.

Processes using certain specific starting materials have also been successful to some extent. Thus, according to German Pat. No. 1,215,365, diaminopolyethers of relatively high molecular weight have been used as the diamine component to prevent the formation of substantially insoluble secondary products. The process according to German Offenlegungsschrift No. 1,963,190 is restricted to the use of diprimary aromatic diamines whose reactivity is reduced by steric or electronic effects. According to British Pat. No. 1,078,390, the formation of insoluble polyureas may be prevented by directly reacting primary diamines with diisocyanates in the presence of a solvent, for example, chloroform. The above process is further restricted to aromatic diamines and also has the disadvantage of the solvent having to be removed on completion of the reaction.

In these conventional processes, formation of the biuret polyisocyanates is accompanied by rearrangement reactions by which the diamine used is converted into the corresponding diisocyanate in dependence upon the $NCO/NH_2$-ratio. As a result, mixtures of different diisocyanates accumulate as distillates during separation of the unreacted diisocyanate from the biuret polyisocyanate unless diamines and diisocyanates of the same constitution are used. Another disadvantage is that more or less large quantities of the diisocyanate formed from the diamine by trans-biuretization remain behind as a monomer conponent in the biuret polyisocyanate itself.

According to German Offenlegungsschrift No. 2,010,887 and U.S. Pat. No. 3,862,973, the direct reaction of secondary diamines may be carried out in particular using aromatic diisocyanates. However, products containing aromatically bound isocyanate groups produced by this known process are unsuitable for high-grade, light-stable lacquers.

Accordingly, an object of the present invention is to provide a process by which it is readily possible to product high-grade, modified, aliphatic polyisocyanates which combine the advantages of known biuret polyisocyanates without the process being attended by the above-mentioned disadvantages.

SUMMARY OF THE INVENTION

According to the present invention, this object is surprisingly achieved by reacting certain aliphatic diamines described in more detail below with excess quantities of certain diisocyanates described in more detail below under certain reaction conditions also described in detail below.

The present invention relates to polyisocyanates corresponding to the formula:

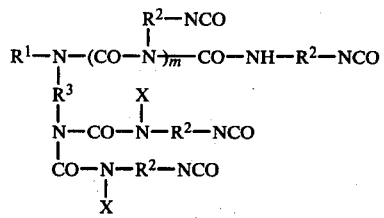

wherein
- $R^1$ represents an aliphatic hydrocarbon radical containing from 1 to 20 carbon atoms or a cycloaliphatic hydrocarbon radical containing from 4 to 20 carbon atoms;

$R^2$ and $R^3$, which may be the same or different, represent aliphatic hydrocarbon radicals having a total of from 2 to 20 carbon atoms optionally containing ester groups or cycloaliphatic hydrocarbon radicals containing from 4 to 20 carbon atoms, at least two carbon atoms being arranged between the two nitrogen atoms;

X represents a radical corresponding to the formula:

$$X = -(CON)_{\overline{m}}H \overset{|}{\underset{}{R^2-NCO}}$$

wherein $R^2$ is defined as defined above; and m and n are each 0 or a number from 0 to 2.

The present invention also relates to a process for producing these polyisocyanates by reacting organic diamines containing hydrogen atoms which are active in the context of the isocyanate addition reaction with excess quantities of organic diisocyanates corresponding to the formula:

$$R^2(NCO)_2$$

characterized in that the diamines used correspond to the formula:

$$R^1-NH-R^3-NH_2$$

wherein the radicals $R^1$, $R^2$, and $R^3$ are as defined above.

The present invention also relates to a modification of this process which is characterized in that organic diamines corresponding to the formula:

$$R^1-NH-R^3-NH_2$$

are reacted in a first stage with excess quantities of a first diisocyanate corresponding to the formula:

$$R^2(NCO)_2$$

after which the thus-obtained reaction product, which contains a urea group and a biuret group, is reacted in a second stage with a second diisocyanate corresponding to the formula:

$$R^2(NCO)_2$$

wherein $R^1$, $R^2$ and $R^3$ are as defined above and further characterized in that $R^2$ in the first diisocyanate is different from $R^2$ in the second diisocyanate.

Furthermore, the present invention also relates to the use of the polyisocyanates, optionally blocked with blocking agents, as the isocyanate component in the production of polyurethane plastics by the isocyanatepolyaddition process.

DETAILED DESCRIPTION OF THE INVENTION

In the above formulae and also in the following, $R^1$, $R^2$, $R^3$, X, m and n are as defined above. These variables preferably have the following meanings:

$R^1$ preferably represents an aliphatic hydrocarbon radical containing from 1 to 4 carbon atoms.

$R^2$ preferably represents an aliphatic hydrocarbon radical containing from 6 to 10 carbon atoms or a cycloaliphatic hydrocarbon radical containing from 6 to 15 carbon atoms, all the radicals $R^2$ preferably having the same meaning.

$R^3$ preferably represents an aliphatic hydrocarbon radical containing from 2 to 10 carbon atoms or a cycloaliphatic hydrocarbon radical containing from 6 to 10 carbon atoms.

m and n each preferably represents 0 or 1.

The polyisocyanates according to the present invention correspond to the above formulae are often mixtures of homologues so that, on a statistical average, m and n may in many cases even represent fractional numbers with values of from 0 to 2. Even in the preferred meaning of the radicals $R^2$ and $R^3$, at least two carbon atoms are always arranged between the two nitrogen atoms.

Starting materials for the process according to the present invention are aliphatic diamines which contain a primary and a secondary amino group, but are otherwise inert under the conditons of the process according to the present invention, and which correspond to the general formula:

$$R_1-NH-R_3-NH_2$$

It is preferred to use diamines corresponding to the above formula which have been obtained by the cyanoethylation of primary monoamines, followed by hydrogenation. Specific examples of such diamines are 1-amino-3-methylaminopropane, 1-amino-3-ethylaminopropane and 1-amino-3-ethylaminopropane and 1-amino-3-propylaminopropane.

However, it is also possible to use representatives of this class of compounds produced by other methods, such as N-methylethylene diamine, N-ethylethylene diamine, 1-amino-4-methylaminobutane, 1-amino-6-methylaminohexane or 2-amino-6-[(N-methyl)-amino]-1-hexane carboxylic acid ethyl ester. It is, of course, also possible to use mixtures of the above-mentioned diamines.

It is particularly preferred to use 1-amino-3-methylaminopropane.

Further starting materials for the process according to the present invention are diisocyanates corresponding to the formula:

$$R^2(NCO)_2$$

Typical examles of such diisocyanates are 1,4-diisocyanatobutane, 1,6-diisocyanatohexane, 2,4,4-trimethyl-1,6-diisocyanatohexane, 1,11-diisocyanatoundecane, 3-isocyanatomethyl-3,5,5-trimethyl cyclohexyl isocyanate, 4,4'-cyclohexane diisocyanate, 4,4'-dicyclohexyl methane diisocyanate, 1,2-bis-(isocyanatomethyl)-cyclobutane or 6-isocyanatocaproic acid-2-isocyanatoethyl ester. It is preferred to use hexamethylene diisocyanate.

As mentioned above, the straightforward reaction of simple organic diamines, such as hexamethylene diamine, and simple diisocyanates, for example, hexamethylene diisocyanate, immediately results in the formation of polyureas which are only slightly soluble in the excess of diisocyanate always used and which may only be converted into corresponding biuret polyisocyanates by prolonged heating in the presence of this diisocyanate excess. However, this prolonged heating results in undesirable discoloration of the reaction products and in other negative side effects. Now, it has surprisingly been found that, by using the diamines according to the present invention as starting materials, it is possible to largely avoid these difficulties so that polyisocyanates according to the present invention corresponding to the above formula, wherein m and n each represents in approximate terms 0, are immediately formed, even in the absence of catalysts. In the absence of catalysts, these triisocyanates, which contain a urea group and a biuret group, react very sluggishly to further quantities of starting diisocyanate. However, it has surprisingly been found that this lack of reactivity may be overcome by using suitable catalysts. The catalysts used in accordance with the present invention are strong proton-releasing acids which react with isocyanates, particularly aliphatic or cycloaliphatic isocyanates, to form a mixed acid anhydride, the carbamic acid corresponding to the isocyanate and the proton-releasing acid representing the acids of the mixed acid anhydride. Thus, such acids HY (Y=acid residue after release of the proton), which are suitable for the process according to the present invention, react with isocyanates Z—NCO to form adducts corresponding to the formula: Z—NH—CO—Y which may be regarded as a mixed anhydride of the carbamic acid Z—NH—COOH and the acid HY.

Examples of suitable acids are hydrogen halides, such as hydrogen fluoride, hydrogen chloride, hydrogen bromide or hydrogen iodide, chlorosulfphonic acid, fluorosulphonic acid, sulphuric acid, alkane, sulphonic acids, such as methane sulphonic acid, or perhalogenated alkane sulphonic acids, such as trifluoromethane sulphonic acid. Hydrogen chloride is the acid preferably used in the process according to the present invention. Instead of using the acids, it is, of course, possible in the process according to the present invention to use both the ammonium salts corresponding to the acids with the amines used as starting materials or the mixed carbamic acid anhydrides corresponding to the acids, particularly carbamic acid chlorides, of the diisocyanates used as starting material or of other isocyanates. The catalysts are generally used in quantities of from about 0.001 to 10%, by weight, preferably from about 0.01 to 1.0%, by weight, based on the total weight of the reactants.

The process according to the present invention may be carried out at temperatures of from about 20° to 250° C. In the absence of the exemplified catalysts, the process is advantageously carried out at from about 140° to 180° C., the end products formed containing urea and biuret groups (m,n,=0). In the presence of the exemplified acids as catalysts, the further reaction beyond this intermediate stage to form addition products containing polyuret groups may be carried out at temperatures of from about 20° to 160° C., the reaction generally taking place quickly at temperatures of from about 90° to 140° C. Accordingly, the catalysts according to the present invention enable isocyanate addition products containing polyuret groups to be produced under mild reaction conditions from aliphatic diisocyanates and aliphatic diamines containing a primary and a secondary amino group adjacent one another or from compounds containing urea groups and biuret groups formed from diamines containing a primary and a secondary amino group adjacent one another and diisocyanates. It is obvious that the catalyst may be added at any time during the reaction. For example, it is possible initially to work at elevated temperature in the absence of catalyst in order to promote the solubility of intermediate stages containing urea groups, which rapidly results in the formation of clear reaction solutions containing products with urea and biuret groups (m,n=0) which are then converted at a lower temperature, but now in the presence of catalyst, into products containing polyuret groups. In cases where the process according to the present invention is carried out using diamines containing a primary and a secondary amino group as starting materials, no readily volatile secondary products are formed. The diamine residue which is inert to the reaction according to the present invention always forms an involatile constituent of the products according to the instant invention. The conversion by trans-biuretization of the primary amino group in the exemplified diamines into an isocyanate group may additionally contribute towards increasing the isocyanate content of the end products.

Where the process of the instant invention is carried out using diamines containing a primary and a secondary amino group as starting materials, these diamines and the diisocyanates are generally used in quantities corresponding to an NCO/NH-molar ratio of from about 2:1 to 100:1 preferably about 2.5:1 to 30:1. Where starting materials containing urea groups and biuret groups are used, the diamines used in accordance with the present invention which are bound therein are included in the calculation of the NCO/NH-molar ratio.

The process of the instant invention is generally carried out as follows:

The diisocyanate is introduced into a suitable reaction vessel and the diamine is added at temperatures of from about 140° to 180° C. The NCO/NH-molar ratio generally amounts to between about 2.5:1 and 30:1. During addition of the amine, slight hazing occurs in the reaction solution disappearing quickly after the amine has been added. A clear solution containing polyisocyanates with urea and biuret groups (m,n=0) is formed.

Unless it is intended to terminate the reaction at this stage, the reaction solution is heated to a temperature of from about 90° to 140° C. and one of the catalysts according to the present invention is added to it to initiate the formation of higher polyuret groups. In the production of polyisocyanates also containing higher polyuret groups, the catalyst may, of course, be added at any stage of the reaction. For example, the catalyst may be initially introduced with the diisocyanate, added with the amines in the form of its ammonium salt or introduced on completion of the preliminary reaction to form intermediate stages containing urea or biuret groups. The reaction mixture is then maintained at a temperature of from about 90° to 140° C. and the course of the reaction is followed by monitoring the reduction in the isocyanate content. Where volatile catalysts, for example, hydrogen chloride, are used, it is possible to work under pressure in order to avoid losses of catalyst which may occur at elevated temperatures and normal pressures.

The reaction is terminated when the reduction in the NCO-content corresponds to the required "degree of polyuretization", i.e., when the required number of NCO-groups per amino group has been reacted. The reaction is terminated simply by cooling the reaction mixture to from about 20° to 50° C. The necessary reaction times are determined by the nature of the starting products, by the temperature and, in particular, by the type and quantity of catalyst used. In general, the reaction time amounts to between about 1 and 5 hours, preferably between about 1 and 2 hours. Clear, colorless to pale yellow reaction solutions are obtained on completion of the reaction.

The reactions are generally terminated at a time when on average, based on the primary and secondary amino group of the diamines used in accordance with the instant invention, a total of about 4 NCO-groups has been consumed. However, it is possible to obtain a higher "degree of polyuretization", i.e., to reaction 5 and more NCO-groups, based on the sum of the amino groups. In that case, however, the viscosities of the products rapidly increase.

The catalyst is generally removed by distilling the reaction mixture in vacuo. Where the catalyst used is a hydrogen halide, it may be even be removed, particularly where it is used in relatively small quantities, by the addition of equimolar quantities of propylene oxide. The catalyst may also be removed, for example, by thin-layer evaporation providing the crude isocyanate is freed from excess diisocyanate. The thin-layer distillate, which in addition to the diisocyanate contains the catalyst, may be reused as starting material.

In cases where it is intended to remove excess diisocyanate, this is generally done by thin-layer evaporation. However, excess diisocyanate may also be removed by extraction with suitable solvents, such as hexane, heptane, etc.

The crude isocyanates may be used as such. In most cases, however, they are preferably freed from isocyanate monomer components by thin-layer evaporation or by extraction. The monomer-free products are pale yellow oils or even solid resins; the NCO-content amounts to between about 5 and 22%, by weight.

The process is particulary suitable for continuous working. To this end, it is possible, for example, to arrange several reaction vessels one behind the other in the form of a cascade. In the first reaction vessel, which may even be replaced by a temperature-controlled static mixer, the starting products diisocyanate and diamine are mixed at from about 140° to 180° C. The catalyst is added to the second reaction vessel at from about 90° to 140° C. if it is desired to obtain reaction products having a relatively high degree of polyuretization. In this case the further reaction by which the polyuret polyisocyanate is formed takes place in the third reaction vessel and in further reaction vessels, if any. The required "degree of polyuretization" being adjusted by controlling the temperature and the residence time. Excess diisocyanate and the catalyst are removed, for example, through a tubular-coil evaporator combined with a following thin-layer evaporator. The distillates consisting of diisocyanate and catalyst are combined, and returned to the process. If desired the catalyst may be removed before the diisocyanate residue is returned to the start of the process. The polyisocyanate is obtained as the thin-layer distillation residue.

In the working of the instant process, the properties of the modified polyisocyanates obtained, particularly the NCO-functionality and NCO-content thereof, and the viscosity thereof may be controlled not only by suitably selecting the starting materials, but also and particularly easily by adjusting the "degree of polyuretization", i.e., the number of NCO-groups reacted per amino group.

In one particular embodiment of the instant process diisocyanates corresponding to the formula:

$$R^2(NCO)_2$$

are used in the first stage of the reaction, which is carried out in the absence of catalysts, the polyisocyanate obtained which contains a urea group and a biuret group is freed from the excess diisocyanate and then subjected to a catalytic further reaction using another diisocyanate corresponding to the formula:

$$R^2(NCO)_2$$

In this case, the radicals $R^2$ are defined the same but the actual radicals are different. In this way, it is possible to produce polyisocyanates according to the present invention containing different $R^2$ radicals.

The end products obtained by the instant process may be used in particular as isocyanate component in the preparation of polyurethane plastics by the isocyanatepolyaddition process. They are suitable both for the preparation of polyurethane foams and also for the preparation of elastomers, coating or adhesives. Where the end products obtained by the process according to the present invention are used for the first of these applications, there is often no need for the excess diisocyanate to be distilled off on completion of the reaction. The monomer-free products obtained by the instant process are excellent starting materials for the production of high-quality, weatherproof and light-stable lacquers. Where the products obtained in accordance with the present invention are used as lacquer-grade polyisocyanates, they are often employed in blocked form, i.e., blocked using known blocking agents. Such blocking agents are, for example, malonic acid diethyl ester ε-caprolactam or acetoacetic acid ethyl ester.

The following Examples serve to illustrate the process of the invention without restricting it in any way. In the Examples all quantities quoted represent percent, by weight, unless otherwise indicated.

EXAMPLE 1

In a 4 liter four-necked flask equipped with a stirrer, reflux condenser and contact thermometer 88 g (1 mole) of 1-amino-3-methylaminopropane were added dropwise over a period of 1 hour at from 140° to 160° C. to 3696 g (22 moles) of 1,6-diisocyanatohexane. The presence of a special nitrogen blanket ensured that the amine added dropwise did not come into contact with isocyanate vapors before entering the reaction solution. The dropwise addition was accompanied by slight clouding of the reaction mixture which quickly passed, into solution. The reaction temperature was then adjusted to from 110° to 120° C. and 4 g of hydrogen chloride were added to the mixture. After 1 hour, the NCO-content of the mixture amounted to 44.3% (corresponding to a consumption of 4.1 NCO-groups, based on the total number of amino groups, i.e., m and n each correspond on a statistical average to (4.1–3:3=0.37)). The reaction solution was cooled to room temperature. Subsequent thin-layer distillation of the clear reaction mixture produced 700 g of a polyisocyanate having an NCO-content of 20.0% and a viscosity of 11500 mPa.s at 20° C.

EXAMPLE 2

Following the procedure of Example 1, 2856 g (17 moles) of 1,6-diisocyanatohexane were reacted with 88 g (1 mole) of 1-amino-3-methylaminopropane over a period of 30 minutes at a temperature of from 160° to 170° C. After the amine had been added, a clear reaction mixture was obtained. The further reaction to form the polyuret polyisocyanate was carried out at from 100° to 110° C. in the presence of 1.5 g of hydrogen chloride. After 1 hour, the NCO-content of the mixture had fallen to 42.8% (corresponding to a consumption of 4 NCO-groups, based on the total number of amino groups). Thin-layer distillation gave 700 g of a polyisocyanate having an NCO-content of 19.6% and a viscosity of 17,500 mPa.s at 20° C.

EXAMPLE 3

Following the procedure of Example 1, 2016 g (12 moles) of 1,6-diisocyanatohexane were reacted with 88 g (1 mole) of 1-amino-3-methylaminopropane over a period of 1 hour at from 170° to 180° C. After cooling to from 100° to 110° C., 1 g of hydrogen chloride was added to the clear reaction mixture. After 1 hour, the NCO-content amounted to 39.9% (corresponding to a consumption of 4 NCO-groups, based on the total number of amino groups). Thin-layer distillation produced 630 g of polyisocyanate (NCO-content=19.5%; viscosity at 20° C.=25400 mPa.s).

EXAMPLE 4

Following the procedure of Example 1, 88 g (1 mole) of 1-amino-3-methylaminopropane were added dropwise over a period of 2 hours at from 120° to 140° C. to 3696 g (22 moles) of 1,6-diisocyanatohexane containing 2 g of hydrogen chloride. Some clouding occurred during the dropwise addition, but passed into solution during the after-reaction. After 2 hours, the reaction mixture was completely clear. The NCO-content amounted to 44.4% (corresponding to a consumption of 4 NCO-groups, based on the total number of amino groups). The reaction mixture was not worked-up any further.

EXAMPLE 5

Following the procedure of Example 1, 3696 g (22 moles) of 1,6-diisocyanatohexane were reacted with 88 g (1 mole) of 1-amino-3-methylaminopropane over a period of 1 hour at from 150° to 160° C. After the reaction solution had turned clear, the temperature was lowered to from 100° to 120° C. 2 g of methane sulphonic acid were then added. After 3 hours, the NCO-content amounted to 44.5% (corresponding to a consumption of 3.9 NCO-groups, based on the total number of amino groups). The reaction mixture was not worked-up any further.

EXAMPLE 6

Following the procedure of Example 1, 2856 g (17 moles) of 1,6-diisocyanatohexane were reacted with 88 g (1 mole) of 1-amino-3-methylaminopropane over a period of 30 minutes at from 160° to 170° C. The NCO-content of the clear reaction solution amount to 44.0% (corresponding to a consumption of 3.1 NCO-groups, based on the total number of amino groups). The reaction mixture was immediately cooled to room temperature. Subsequent thin-layer distillation produced 520 g of a biuret polyisocyanate having an NCO-content of 19.9% and a viscosity of 7000 mPa.s at 20° C.

EXAMPLE 7

Following the procedure of Example 1, 4884 g (22 moles) of isophorone diisocyanate were reacted with 88 g (1 mole) of 1-amino-3-methylaminopropane over a period of 1 hour at from 150° to 160° C. in a 6 liter flask. The NCO-content of the clear reaction solution amounted to 34.6% (corresponding to consumption of 3.1 NCO-groups, based on the total number of amino groups). The excess diisocyanate was not removed.

EXAMPLE 8

(Application Example)

Following the addition of 0.5 g of a tertiary amine as catalyst and 0.4 g of cellulose butyrate propionate as levelling agent, 77 g of a 65% solution of a highly branched polyester based on phthalic acid anhydride and trimethylol propane (hydroxyl content 8%) in ethylglycol acetate/xylene (1:1) were diluted with 100 g of a solvent mixture of methylethyl ketone, butyl acetate, ethyl glycol acetate and toluene (4:1:4:1) 65.9 g of a 75% solution of the polyisocyanate of Example 1 in ethyl glycol acetate/xylene (1:1) were then added (NCO:OH ratio=1:1). The lacquer solution obtained was then applied to steel plates where the lacquer films hardened at room temperature. The hardened clear lacquer films were scratch-resistant, elastic and resistant to solvents, such as toluene, ethyl glycol acetate, ethyl acetate or acetone. In addition, they had the following properties:

| layer thickness | approx. 40μ |
|---|---|
| Erichsen indentation (DIN 53 156) | |
| after 3 days | 9.8 mm |
| after 7 days | 9.0 mm |
| pendulum hardness (DIN 53 157) | |
| after 3 days | 147 seconds |
| after 7 days | 169 seconds |

EXAMPLE 9

(Application Example)

Following the addition of 0.5 g of a tertiary amine as catalyst and 0.4 g of cellulose butyrate propionate as levelling agent, 77 g of a 65% solution of a highly branched polyester based on phthalic acid anhydride and trimethylol propane (hydroxyl content 8%) in ethyl glycol acetate/xylene (1:1) were diluted with 100 g of a solvent mixture of methylethyl ketone, butyl acetate, ethyl glycol acetate and toluene (4:1:4:1). 65.9 g of a 75% solution of the polyisocyanate of Example 6 in ethyl glycol acetate/xylene (1:1) were then added (NCO:OH-molar ratio=1:1). The lacquer solution obtained was then applied to steel plates where the lacquer films hardened at room temperature. The hardened clear lacquer films were scratch-resistant, elastic, and resistant to solvent such as toluene, ethyl glycol acetate, ethyl acetate or acetone. In addition, they had the following properties:

| layer thickness | approx. 50μ |
|---|---|
| Erichsen indentation (DIN 53 156) | |
| after 3 days | 9.6 mm |
| after 7 days | 9.0 mm |
| pendulum hardness (DIN 53 157) | |

-continued

| | |
|---|---|
| after 3 days | 146 seconds |
| after 7 days | 182 seconds |

EXAMPLE 10

(Application Example)

77 g of the polyester solution described in Example 8 were processed with 50 g of titanium dioxide (rutile) to form a paste. In addition to catalyst and levelling agent, 50 g of the above-described solvent mixture were added to the thus-obtained paste. 65.9 g of a 75% solution of the polyisocyanate of Example 1 in ethyl glycol acetate/xylene (1:1) were added to the resulting mixture which was then applied in thin layers to steel plates. The pigment-containing lacquer films hardened at room temperature. They were distinguished by resistance to scratching and solvents and, compared with the clear lacquer films, had the following properties:

| | |
|---|---|
| layer thickness | approx. 50µ |
| Erichsen indentation (DIN 53 156) | |
| after 3 days | 10.0 mm |
| pendulum hardness (DIN 53 157) | |
| after 3 days | 91 seconds |
| after 7 days | 120 seconds |

EXAMPLE 11

(Application Example)

77 g of the polyester solution described in Example 8 were processed with 50 g of titanium dioxide (rutile) to form a paste. In addition to catalyst and levelling agent, 50 g of the above-described solvent mixture were added to the resulting paste. 65.9 g of a 75% solution of the polyisocyanate of Example 6 in ethyl glycol acetate/xylene (1:1) were added to the resulting mixture which was then applied in thin layers to steel plates. The pigment-containing lacquer films hardened at room temperature. They were distinguished by resistance to scratching and solvents and, compared with the clear lacquer films, had the following properties:

| | |
|---|---|
| layer thickness | approx. 50µ |
| Erichsen indentation (DIN 53 156) | |
| after 3 days | 10.1 mm |
| pendulum hardness (DIN 53 157) | |
| after 3 days | 90 seconds |
| after 7 days | 112 seconds |

What is claimed is:

1. A polyisocyanate corresponding to the formula:

$$R_1-N(-CO-N\frac{}{m}-CO-NH-R_2-NCO$$
$$\begin{array}{cc} | & | \\ R_3 & X \\ | & | \\ N-CO-N-R_2-NCO \\ | \\ CO-N-R_2-NCO \\ | \\ X \end{array}$$
$$\begin{array}{c} | \\ R_2-NCO \end{array}$$

wherein
$R_1$ represents an aliphatic hydrocarbon radical selected from the group consisting of methyl, ethyl and propyl;
$R_2$ represents hexamethylene;
$R_3$ represents propylene;
X represents a radcial corresponding to the formula:

$$X = (-CO-N\frac{}{n})H$$
$$\begin{array}{c} | \\ R_2-NCO \end{array}$$

and m and n are each 0 or a number from 0 to 2.

2. A process for producing polyisocyanates corresponding to the formula:

$$R_1-N(-CO-N\frac{}{m}-CO-NH-R_2-NCO$$
$$\begin{array}{cc} | & | \\ R_3 & X \\ | & | \\ N-CO-N-R_2-NCO \\ | \\ CO-N-R_2-NCO \\ | \\ X \end{array}$$
$$\begin{array}{c} | \\ R_2-NCO) \end{array}$$

wherein X represents a radical corresponding to the formula:

$$X = (-CO-N\frac{}{n})H$$
$$\begin{array}{c} | \\ R_2-NCO \end{array}$$

and m and n are each 0 or a number from 0 to 2, comprising: reacting organic diamines containing hydrogen atoms which are active in the context of the isocyanate addition reaction with excess quantities of a diisocyanate corresponding to the formula:

$$R_2(NCO)_2$$

characterized in that said diamines used correspond to the formula:

$$R_1-NH-R_3-NH_2$$

wherein
$R_1$ represents an aliphatic hydrocarbon radical selected from the group consisting of methyl, ethyl and propyl;
$R_2$ represents hexamethylene; and
$R_3$ represents propylene.

3. A process as claimed in claim 2 characterized in that said reactions are carried out in the presence of catalytic quantities of strong acids which form mixed carbamic acid anhydrides with isocyanates.

4. In a process for producing polyurethane by reacting a polyisocyanate with active hydrogen containing materials, the improvement wherein said polyisocyanate is the polyisocyanate of claim 1, optionally blocked with blocking agents.

* * * * *